(12) United States Patent
Holmén et al.

(10) Patent No.: US 12,648,877 B2
(45) Date of Patent: Jun. 9, 2026

(54) NEGATIVE PRESSURE WOUND THERAPY (NPWT) DRESSING

(71) Applicant: Mölnlycke Health Care AB, Gothenburg (SE)

(72) Inventors: Malin Holmén, Gothenburg (SE); Elinor Bolyos, Landvetter (SE)

(73) Assignee: Mölnlycke Health Care AB, Mölndal (SE)

( * ) Notice: Subject to any disclaimer, the term of this patent is extended or adjusted under 35 U.S.C. 154(b) by 331 days.

(21) Appl. No.: 18/568,496

(22) PCT Filed: Jun. 20, 2022

(86) PCT No.: PCT/EP2022/066759
§ 371 (c)(1),
(2) Date: Dec. 8, 2023

(87) PCT Pub. No.: WO2022/268737
PCT Pub. Date: Dec. 29, 2022

(65) Prior Publication Data
US 2025/0000709 A1 Jan. 2, 2025

(30) Foreign Application Priority Data
Jun. 22, 2021 (EP) .................................... 21180831

(51) Int. Cl.
A61F 13/0206 (2024.01)

(52) U.S. Cl.
CPC ................................ A61F 13/0209 (2013.01)

(58) Field of Classification Search
CPC .... A61F 13/05; A61F 13/0209; A61F 13/022; A61F 13/0206; A61F 13/01029; A61F 2013/00536; A61F 13/00; A61F 13/01021; A61F 13/02; A61F 13/0226; A61F 2013/00246; A61M 1/915; A61M 1/90; A61M 1/912; A61M 1/913; A61M 27/00; A61M 2205/75; A61M 2205/7563
See application file for complete search history.

(56) References Cited

U.S. PATENT DOCUMENTS 5,556,375 A * 9/1996 Ewall .................. A61F 13/0203
602/54
6,071,267 A * 6/2000 Zamierowski ........ A61M 1/964
604/289

(Continued)

FOREIGN PATENT DOCUMENTS

EP 3207905 A1 8/2017

OTHER PUBLICATIONS

International Search Report and Written Opinion were mailed on Dec. 16, 2022 by the International Searching Authority for International Application No. PCT/EP2022/066759 filed on Jun. 20, 2022 and published as WO/2022/268737 (Applicant—Molnlycke Health Care AB) (9 pages).

*Primary Examiner* — Adam Marcetich
(74) *Attorney, Agent, or Firm* — Ballard Spahr LLP

(57) ABSTRACT
Described is a negative pressure wound therapy (NPWT) dressing with a wound pad comprising two separate wound pad portions having different properties. Also described is a portable negative pressure wound therapy (NPWT) system that includes the described negative pressure wound therapy (NPWT) dressing.

17 Claims, 4 Drawing Sheets

(56) References Cited

U.S. PATENT DOCUMENTS

| | | | | |
|---|---|---|---|---|
| 2002/0115952 | A1* | 8/2002 | Johnson | A61M 1/985 |
| | | | | 602/41 |
| 2007/0265586 | A1* | 11/2007 | Joshi | A61M 1/78 |
| | | | | 604/313 |
| 2009/0299303 | A1* | 12/2009 | Seegert | A61M 1/915 |
| | | | | 602/53 |
| 2010/0069858 | A1* | 3/2010 | Olson | A61M 1/915 |
| | | | | 604/319 |
| 2010/0125233 | A1* | 5/2010 | Edward S. | A61F 13/00991 |
| | | | | 602/42 |
| 2010/0179515 | A1* | 7/2010 | Swain | A61B 17/11 |
| | | | | 514/6.9 |
| 2012/0041403 | A1* | 2/2012 | Bennett | A61M 1/915 |
| | | | | 604/319 |
| 2013/0131564 | A1* | 5/2013 | Locke | A61F 13/05 |
| | | | | 601/149 |
| 2014/0276491 | A1* | 9/2014 | Luckemeyer | A61F 13/025 |
| | | | | 604/319 |
| 2015/0202353 | A1* | 7/2015 | Daughtery | A61M 1/98 |
| | | | | 604/319 |
| 2017/0189236 | A1* | 7/2017 | Locke | A61F 13/01029 |
| 2019/0015258 | A1* | 1/2019 | Gowans | A61F 13/05 |
| 2019/0030224 | A1* | 1/2019 | Lin | A61M 1/94 |
| 2019/0159938 | A1* | 5/2019 | Askem | A61M 1/784 |
| 2020/0023106 | A1* | 1/2020 | Carroll | A61F 13/05 |
| 2021/0052432 | A1* | 2/2021 | Buan | A61F 13/022 |
| 2021/0137743 | A1 | 5/2021 | Yerbury et al. | |
| 2022/0008642 | A1* | 1/2022 | Waite | A61B 10/0045 |
| 2022/0355021 | A1* | 11/2022 | Locke | A61M 1/915 |
| 2023/0038460 | A1* | 2/2023 | Long | A61M 1/915 |

* cited by examiner

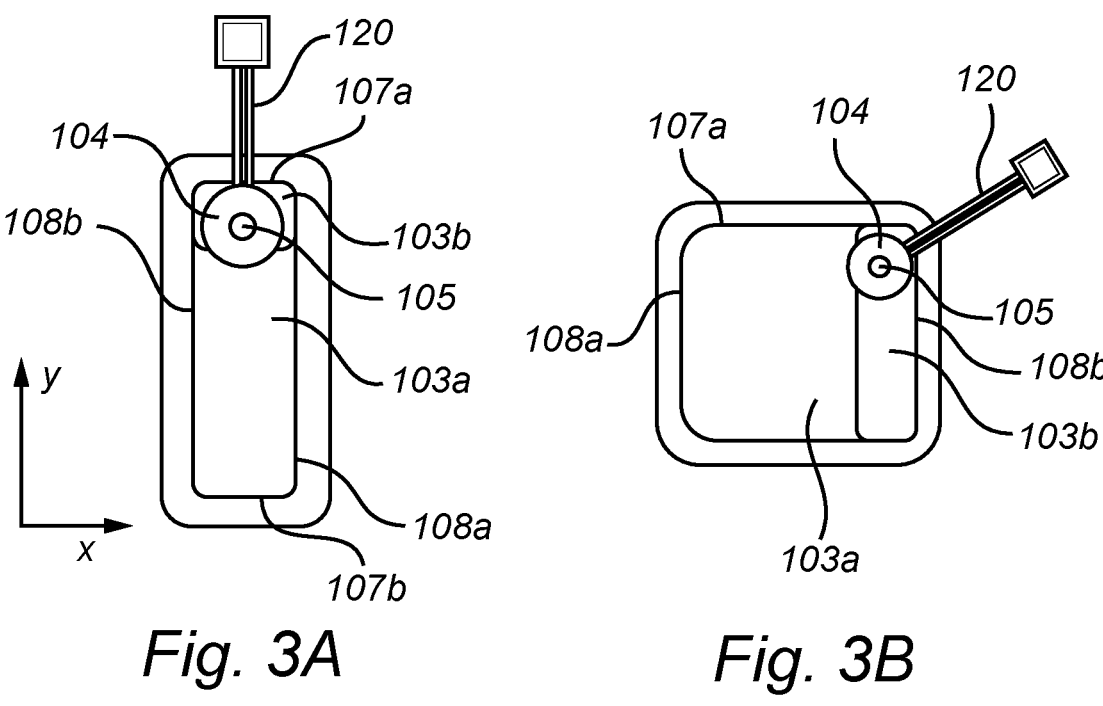
*Fig. 3A*          *Fig. 3B*
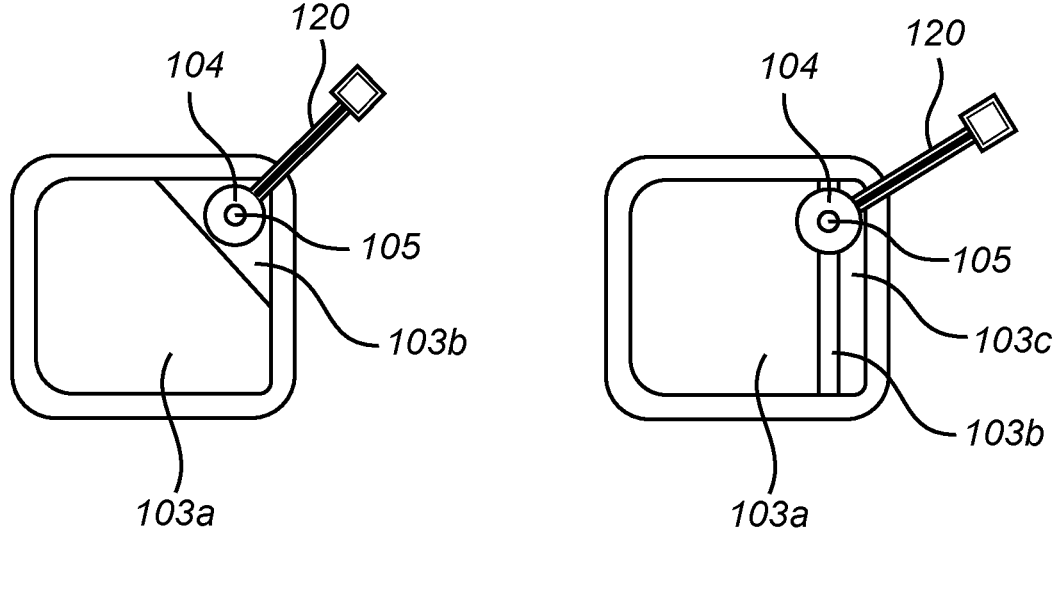
*Fig. 3C*          *Fig. 3D*

NEGATIVE PRESSURE WOUND THERAPY (NPWT) DRESSING

CROSS REFERENCE TO RELATED APPLICATIONS

This application is a U.S. National Phase Application of International Application No. PCT/EP2022/066759, filed Jun. 20, 2022, which claims priority to European Patent Application No. 21180831.6, filed Jun. 22, 2021, each of which are hereby incorporated by reference in their entirety.

TECHNICAL FIELD

The present disclosure generally relates to a negative pressure wound therapy (NPWT) dressing with a wound pad comprising two separate wound pad portions. The present disclosure also relates to a portable negative pressure wound therapy (NPWT) system comprising such a dressing.

BACKGROUND

Negative pressure wound therapy (NPWT) is a technique that promotes healing of e.g. surgical, acute and chronic wounds by the application of a sub-atmospheric pressure to the wound, using a negative pressure pump. Wound healing is achieved by applying a negative pressure, such as vacuum through a dressing or a cover applied onto the wound. Excess wound exudate is thereby drawn out, which increases the blood flow to the area, and promotes the formation of granulation tissue. The NPWT technique also permits less outside disturbance of the wound and transports excess fluid away from the wound site.

The NPWT technique has, until now, mainly been applied to a patient while in a hospital environment. However, recent product development allows the technique to be used by a patient in a home environment.

In a home environment, a portable NPWT system, which may be carried around by the patient, is generally preferred. A portable NPWT system typically comprises an absorbent dressing configured to be connected to a negative pressure source by means of a tubing. An NPWT system comprising an absorbent dressing may also be utilized in a hospital or care facility.

An absorbent dressing for use in a portable NPWT system typically comprises a transmission layer, such as a spacer fabric material, that serves to facilitate the transmission of negative pressure from the negative pressure source, which is typically a vacuum pump, to the wound site Furthermore, a dressing for use in a portable NPWT system typically comprises an absorbent wound pad configured to handle, and store wound fluid exuded from the wound. In some NPWT systems, the absorbent dressing serves as the sole means for fluid handling and storage of wound exudate, whereas in other systems, a remote fluid collection means, such as a canister, is connected to the dressing such that at least a part of the wound exudate is transferred to the canister. In such cases, both the dressing and the canister are configured to store wound exudate.

The negative pressure source is fluidly connected to the absorbent dressing by means of a tubing that may be firmly attached or detachably attached to the dressing. Usually, the tubing is connected to a coupling portion provided on the backing layer of the dressing. To enable fluid communication between the negative pressure source and the dressing, an orifice is usually provided in the backing layer in the area where the coupling member is attached.

In order to improve the fluid communication between the wound site and the negative pressure source and to secure sufficient negative pressure transmission, the area of the absorbent wound pad underlying the coupling portion often comprises an orifice that extends through the entire absorbent wound pad or through a part of the absorbent wound pad. The orifice secures that negative pressure is transmitted to the wound site in an efficient manner. Accordingly, the orifice prevents the absorbent wound pad from blocking the transmission of negative pressure to the wound site.

From a manufacturing point of view, the provision of an orifice in the absorbent wound pad, is associated with complex processability and high costs. For example, the orifice must be aligned with the orifice provided in the backing layer, where the coupling portion is attached.

There is therefore a need to provide an absorbent dressing for use in negative wound therapy that is easy and inexpensive to produce. Such a dressing should secure efficient transmission of negative pressure to the wound site while also ensuring that wound exudate is properly handled and distributed within the dressing.

SUMMARY OF THE INVENTION

In view of the above mentioned problems, it is an object of the present disclosure to provide improvements with respect to dressings for negative pressure wound therapy (NPWT) applications, particularly with respect to improving the processability of such dressing while securing an appropriate balance between transmission of negative pressure and wound exudate handling by the dressing.

According to a first aspect of the present disclosure, there is provided a negative pressure wound therapy (NPWT) dressing comprising a backing layer, an adhesive skin contact layer and a wound pad arranged between the backing layer and the adhesive skin contact layer, wherein the backing layer comprises a coupling member configured to connect the dressing to a negative pressure source, wherein the backing layer comprises an opening in the area where the coupling member is attached, wherein the wound pad comprises a first portion comprising one or more absorbent layers and a second portion comprising at least one transmission layer, wherein the second portion of the wound pad is arranged below the coupling member.

Accordingly, the second wound pad portion arranged below the coupling member is void of an opening. The dressing of the present disclosure may be manufactured in a simplified manner since no material needs to be removed from the wound pad or from the dressing interior structure. Instead of providing an opening in the area below the coupling member and aligning such an opening with the opening in the backing layer, as is typically the case with dressings for use in negative pressure wound therapy, the transmission of negative pressure to the wound site is secured through the second portion of the wound pad. Accordingly, the wound pad comprises two distinct portions having different properties and characteristics.

Typically, the second portion of the wound pad consists of one or two transmission layers.

The first portion of the wound pad is absorbent and is configured to handle, store and distribute the wound liquid exuded from the wound. The second portion comprising at least one transmission layer is configured to secure transmission of negative pressure to the wound site and also to secure fluid communication between the wound site and the negative pressure source (through the coupling member and any tubing connected thereto).

The second portion comprises no absorbent layers. The second portion is regarded as substantially non-absorbent. The presence of absorbent layers below the coupling member could block the fluid communication from the wound site or the transmission of negative pressure to the wound site. Accordingly, with a dressing according to the present disclosure, no obstruction or interruption between the wound site and the coupling member is present.

The first and the second portion of the wound pad are typically coplanar; i.e. arranged in the same plane The first portion and the second portion of the wound pad may form two distinct, juxtaposed portions arranged in the same plane of the wound pad.

Accordingly, the first and the second portions of the wound pad are disposed in a side-by-side arrangement.

The first and the second portion are formed from two (or more) different materials having different properties. The first and the second portion may be attached or unattached to one another. Typically, the first and the second portions are arranged to contact each other but are unattached. The first and the second portions are disposed such that substantially no gap is formed between the portions.

In exemplary embodiments, the first and the second portion of the wound pad have substantially the same thickness.

In exemplary embodiments, the first portion of the wound pad comprises a superabsorbent material, preferably superabsorbent particles, wherein the second portion of the wound pad is void of a superabsorbent material.

A superabsorbent material, such as superabsorbent particles is advantageously used in the first portion of the wound pad. This is to facilitate the handling of large amounts of wound exudate, typically associated with wounds in need of negative pressure wound therapy.

Superabsorbent particles are formed from superabsorbent polymers (SAP) that are capable of absorbing large quantities of fluid upon the formation of a hydrogel. The second portion of the wound pad is void of any superabsorbent particles. This is to prevent potential gelling superabsorbent particles (and undesired larger particulate of the wound exudate) from blocking the transmission of negative pressure and from entering the coupling member, and the tubing connecting the coupling member with a negative pressure source. It is also conceivable that the superabsorbent layer comprises superabsorbent fibers (SAF).

In exemplary embodiments, the first portion constitutes of from 60% to 95%, preferably from 70% to 85% of the surface area of the wound pad.

This is beneficial to secure that the wound exudate is absorbed, stored, and distributed in an efficient manner. The first portion of the wound pad functions as a reservoir to retain and distribute exudate. If the second, non-absorbent, portion of the wound pad is larger or constitutes "too much" of the wound pad, this could lead to a too quick flow of liquid from the wound site to the backing layer and a saturation of liquid within the dressing. As a consequence, the adhesive layer may lose its adhesion to the skin such that the dressing must be discarded. Accordingly, the fact that the first portion constitutes a significantly larger part of the wound pad improves the wear time of the dressing.

In exemplary embodiments, the wound pad comprises a central portion and an edge portion surrounding the central portion, and wherein the second portion is arranged in the edge portion of the wound pad.

Accordingly, the coupling member is attached to the backing layer in an area overlying the edge portion of the wound pad. This arrangement is beneficial from a manufacturing point of view.

In exemplary embodiments, the second portion of the wound pad is configured to extend across at least 60%, preferably at least 75%, more preferably at least 90% of the cross-sectional area of the opening in the backing layer.

In order to secure the transmission of negative pressure and to avoid potential blockage of such transmission, the area of the wound pad below the opening (and the coupling member) is comprised of the second portion of the wound pad. It is beneficial, but not necessary that the second portion of the wound pad extends across the entire cross-sectional area of the opening. At least 60%, preferably at least 75%, more preferably at least 90% of the cross-sectional area of the opening in the backing layer is "covered" by the second portion. This is to secure sufficient transmission of negative pressure to the wound site and to balance such transmission with an efficient absorbent capacity provided by the first (absorbent) portion of the wound pad.

The dressing of the present disclosure is not limited to a specific shape or size. However, in embodiments, the wound pad has a lateral (x) and a longitudinal (y) extension and wherein the wound pad is contoured by a pair of lateral edges extending in parallel to each other in the longitudinal direction and a pair of longitudinal edges extending in parallel to each other in the lateral direction, wherein the second portion of the wound pad is arranged along one of the lateral edges or one of the longitudinal edges of the wound pad.

This arrangement is beneficial for manufacturing purposes. In cases where the dressing is square shaped, it does not matter whether the second portion of the wound pad forms the lateral edge or the longitudinal edge. In the case of a rectangular dressing, the second portion of the wound pad typically forms the longitudinal edge of the dressing; i.e. the edge of the dressing having the smallest extension; i.e. width.

In exemplary embodiments, the transmission layer of the second portion of the wound pad comprises a spacer fabric material.

A spacer fabric is a three dimensional material that is advantageously utilized in negative pressure wound therapy (NPWT) dressings for the purpose of transmitting negative pressure to the wound site. A spacer fabric transmission layer is resistant to compression and is configured to withstand pressures exerted on the dressing during use. After a compressive force has been exerted to the dressing, the transmission layer is configured to return to its original shape immediately after removal of the force. A spacer fabric layer has the function of transmitting negative pressure and to transport, but not absorb, liquid; i.e. wound exudate. In exemplary embodiments, the dressing further comprises a liquid spreading layer arranged between the backing layer and the wound pad.

The provision of a liquid spreading layer between the wound pad and the backing layer provides several advantages in terms of liquid handling and liquid distribution.

The liquid spreading layer improves the spreading and distribution of wound exudate within the dressing, thereby forming a larger surface area from which exudate can evaporate from the dressing (through the backing layer).

In embodiments where the dressing is used in negative pressure wound therapy (NPWT) system comprising a remote fluid collection means, e.g. a canister, the provision of a liquid distribution layer has the additional function of distributing potential "backflow" exudate; i.e. exudate flowing in the opposite direction (from the canister to the dressing by means of the tubing connecting these). This may for example occur if the dressing is disconnected from the negative pressure source and/or the canister. The liquid spreading layer secures that such back-flow of exudate is spread out rather than flowing back towards the wound site in one spot. This way, the wound site can be kept relatively dry.

In such embodiments, where fluid storage is provided by both the wound dressing and a canister, the liquid spreading layer furthermore contributes to a controlled and balanced liquid distribution between the dressing and the canister. The dressing's ability to function as a fluid collection means is optimized, while still allowing for the removal and transport of a substantial portion of exudate from the dressing.

In exemplary embodiments, the liquid spreading layer is configured to extend across at least 90% of the surface area of the wound pad and wherein the liquid spreading layer is void of an opening.

The liquid spreading layer is void of an opening and is arranged to extend across; i.e. below, the opening provided in the backing layer. Accordingly, potential gelling particles and undesired larger particulate of the exudate are prevented from entering the coupling member and the tubing connecting the dressing with the negative pressure source (and canister, where present). The liquid spreading layer is configured to transfer and distribute liquid absorbed by the first (absorbent) portion of the wound pad, and, in embodiments, secure the transfer of liquid to a remote fluid collection means.

In exemplary embodiments, the liquid spreading layer comprises a nonwoven.

A nonwoven imparts an appropriately balanced rigidity to the layer and to the dressing as such. A nonwoven liquid spreading layer has the ability to distribute fluid throughout the majority of the material and to transfer the exudate in a controlled manner to the coupling member and the tubing connecting the dressing with a remotely arranged fluid collection means, if present.

Typically, the at least one transmission layer of the second portion is arranged in contact with the liquid spreading layer.

Accordingly, wound exudate transferred from the wound site through the second portion of the wound pad will be distributed and spread efficiently, and potential larger particulates will be prevented from entering the tubing of the NPWT system.

In exemplary embodiments, the transmission layer of the second portion of the wound pad is a first transmission layer and wherein the dressing further comprises a second transmission layer, preferably comprising a spacer fabric, between the adhesive skin contact layer and the wound pad.

The area of the dressing underlying the coupling member may thus be provided with two transmission layers arranged on top of each other (a first transmission layer of the second portion of the wound pad and an underlying second transmission layer). This construction improves the transmission of negative pressure, and furthermore improves the liquid transport from the wound site to the tubing and to the interior of the first portion of the wound pad that is configured to store and distribute the exudate.

In exemplary embodiments, the second transmission layer is arranged between the adhesive layer and the first portion of the wound pad, and wherein the second portion of the wound pad has a thickness corresponding to the thickness of the first portion of the wound pad and the second transmission layer.

Accordingly, the dressing is provided with two, juxtaposed transmission layers. The second transmission layer is arranged below the first portion of the wound pad, and the first, thicker, transmission layer is provided in the area underlying the coupling member. Hence, the second transmission layer forms part of the second portion of the wound pad.

In exemplary embodiments, the first portion of the wound pad comprises a first liquid distribution layer, a superabsorbent layer and a second liquid distribution layer, wherein the superabsorbent layer is arranged between the first and the second liquid distribution layers.

The superabsorbent layer is configured to absorb and temporarily retain exudate. The superabsorbent layer preferably comprises superabsorbent polymer particles capable of absorbing large quantities of fluid upon formation of a hydrogel.

Wound exudate flowing from the wound site is first distributed across the area of the first liquid distribution layer before being absorbed by the superabsorbent layer. The second liquid distribution layer distributes the exudate from the superabsorbent layer such that the exudate is spread over a large area before being evaporated from the backing layer.

According to a second aspect, there is provided a portable negative pressure wound therapy (NPWT) system comprising:

a negative pressure wound therapy (NPWT) dressing as described hereinbefore, a negative pressure source fluidly connected to the dressing.

In exemplary embodiments, the system further comprises a remote fluid collection means, such as a canister, fluidly connected to the negative pressure source and to the dressing.

Accordingly, the portable negative pressure system comprises two exudate storage means; i.e. the first absorbent portion of the wound pad as well as a remote fluid collection means, e.g. a canister. This is beneficial to avoid exudate saturation within the dressing, which could ultimately lead to loss of adhesion to the skin. The provision of a canister may thus enhance the wear time of the dressing since two separate fluid handling systems are comprised in the NPWT system.

In exemplary embodiments, the portable NPWT system comprises means to supply air to the dressing at a rate of from 2 to 7 ml/min during operation A small and controlled inflow of air may be beneficial to more efficiently draw fluid from the wound site and transport the fluid to the remotely arranged fluid collection means, e.g. the canister. It may also be beneficial to avoid potential obstructions in the tubing connecting the dressing with the negative pressure source and the remote fluid collection means and to secure that the desired pressure level is transmitted to the wound site. In negative pressure wound therapy systems, there typically a static pressure difference introduced by gravity between the pressure inside the canister and the pressure at the wound site. This is due to the height difference between the canister and the wound site. A change in the static pressure may affect the ability to provide the correct level of negative pressure at the wound site. The provision of a small air flow or air leakage resolves these problems. Furthermore, if too much air is introduced, this may negatively impact the stability of the system, and the pump must typically be activated on a higher frequency.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF DRAWINGS

The various aspects of the present disclosure, including its particular features and advantages, will be readily understood from the following detailed description and the accompanying drawings, in which:

FIG. 1b illustrates a cross-sectional view of the dressing of FIG. 1a.

FIGS. 3a-d illustrate exemplary embodiments of a dressing according to the present disclosure, showing alternative arrangements of the first and second portions of the wound pad.

DETAILED DESCRIPTION

Figure 1A:
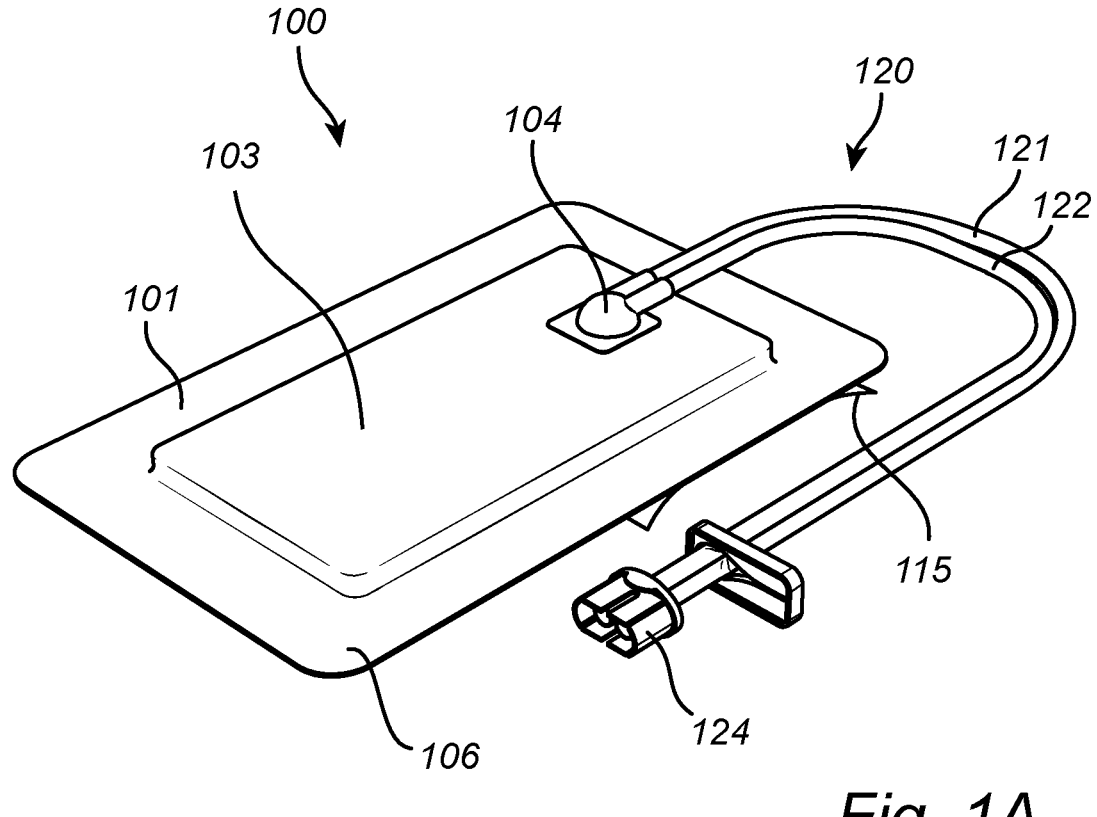
FIG. 1a schematically illustrates a dressing according to an exemplary embodiment of the present disclosure.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Figure 1B:
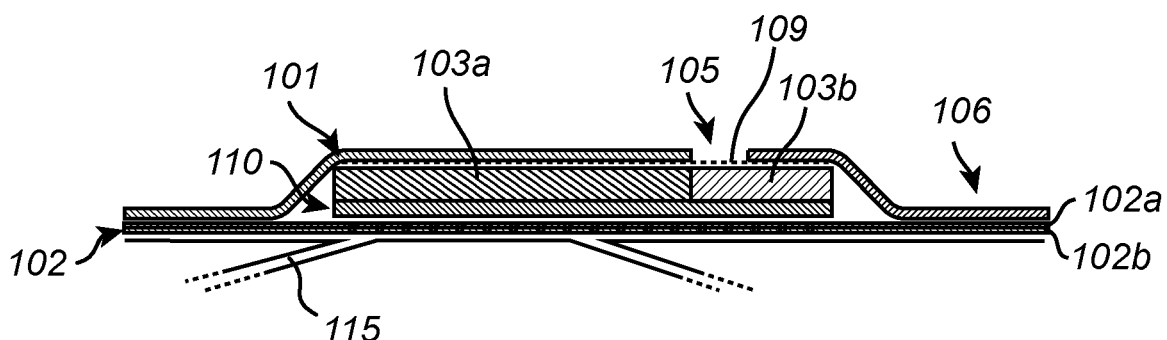

FIGS. 1a and 1b illustrate a negative pressure wound therapy (NPWT) dressing 100 comprising a backing layer 101, an adhesive skin contact layer 102 and a wound pad 103 arranged between the backing layer 101 and the adhesive skin contact layer 102, wherein the backing layer 101 comprises a coupling member 104 configured to connect the dressing to a negative pressure source, wherein the backing layer 101 comprises an opening 105 in the area where the coupling member 104 is attached, wherein the wound pad 103 comprises a first portion 103a comprising one or more absorbent layers and a second portion 103b comprising at least one transmission layer, wherein the second portion 103b of the wound pad 103 is arranged below the coupling member 104.

As used herein, the term "negative pressure wound therapy dressing" refers to a dressing for use in negative pressure wound therapy. In the context of the present disclosure, "negative pressure wound therapy" refers to a therapy utilizing a source of negative pressure (e.g. a vacuum pump) to remove excess fluid from a wound. The wound may be an open wound or it may be a closed wound; i.e. a surgically closed incision, and the term therefore also encompasses "topical negative pressure (TNP) therapy" applications, which is a term often used in the context of closed incisions.

The NPWT dressing 100 of the present disclosure may be referred to as "bordered dressing". As illustrated in FIG. 1, the backing layer 101 and the adhesive skin contact layer 102 are arranged to extend beyond the contour of the wound pad 103 to form a border portion 106.

As used herein, the term "transmission layer" refers to a layer configured to transmit negative pressure to the wound site. The transmission layer is generally non-absorbent; i.e. it may transport wound exudate, but is typically not configured to absorb wound exudate. The transmission layer is not limited to a particular material, but any material configured to ensure that negative pressure can be transmitted to the wound area during both wet and dry conditions can be used. Typically, the transmission layer comprises a spacer fabric material.

The second portion 103b of the wound pad 103 is "arranged below" the coupling member 104. This does not imply that the second portion is arranged in direct contact with the coupling member 104. In embodiments, a liquid spreading layer is arranged between the backing layer and the wound pad, and consequently between the coupling member and the second portion of the wound pad.

Figure 2:
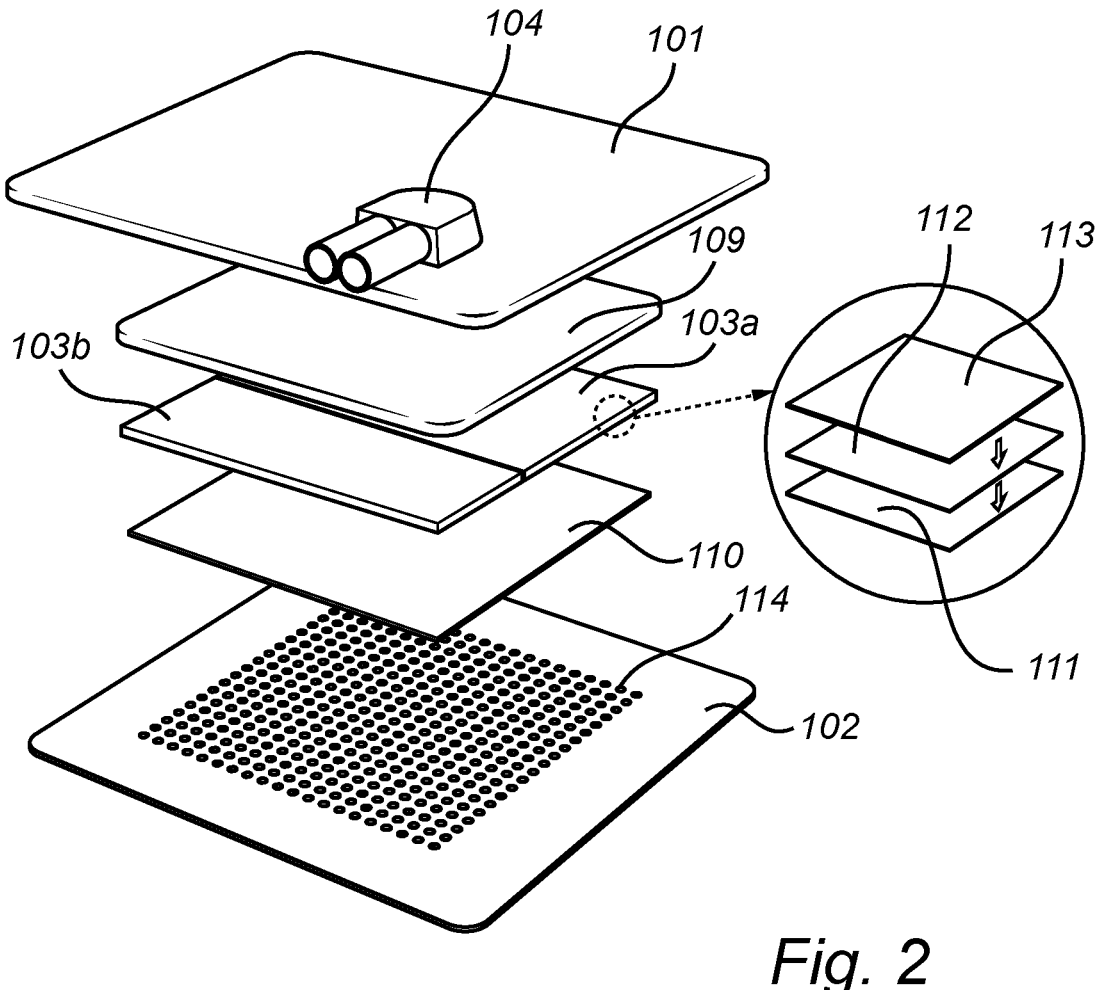
FIG. 2 is a split view of a dressing according to an exemplary embodiment of the present disclosure.

As best illustrated in FIG. 1b and FIG. 2, the first portion 103a and the second portion 103b of the wound pad 103 form two juxtaposed portions disposed in a side-by-side arrangement. The first portion 103a and the second portion 103b of the wound pad may be arranged in the same plane of the wound pad 103.

In FIGS. 1b and 2, the first 103a and the second portion 103b of the wound pad are coplanar; i.e. arranged in the same plane. The thickness of the first and the second portion may be the same. Accordingly, the dressing 100 has a generally even construction without any protrusions or protuberances on the surface of the dressing.

The first 103a and the second 103b portions of the wound pad form two distinct portions that are arranged such that substantially no gap is formed between the portions. The first 103a and the second portion 103b of the wound pad are typically arranged to contact each other, but are not attached. During manufacturing, the first and the second portions are aligned and arranged such that the portions contact each other in a side-by-side relationship. Gaps larger than 3 mm are considered undesired since such gaps may yield an uneven dressing surface, and a too quick flow of wound exudate from the wound site towards the backing layer; i.e. the outer surface of the dressing. Preferably, the gap between the first and the second portions is less than 2 mm, e.g. less than 1 mm.

The provision of two different portions in the wound pad provides for an optimized construction, wherein the first, absorbent portion 103a of the wound pad serves the function of improving the liquid handling, storage and distribution of wound exudate, whereas the second portion 103b of the wound pad serves to improve the fluid communication and the transmission of negative pressure to the wound site. It also significantly simplifies the manufacturing process.

The first portion 103a of the wound pad 103 may comprise a superabsorbent material, such as superabsorbent particles, whereas the second portion 103b of the wound pad 103 is void of a superabsorbent material.

Accordingly, the potential blocking effect that gelling SAP particles could give rise to is avoided in the area where transmission of negative pressure is to be provided. The superabsorbent material may also be in the form of fibers; i.e. superabsorbent fibers (SAF).

Since wounds in need of negative pressure wound therapy are typically regarded as medium to highly exuding wounds, it is important to secure efficient liquid handling within the dressing.

Accordingly, the first portion 103a may constitute of from 60% to 95%, preferably from 70% to 85% of the surface area of the wound pad 103.

Wound exudate is thereby managed in a sophisticated and controlled manner by a large portion of the wound pad.

The second portion 103b may constitute of from 5 to 40%, preferably from 15 to 30% of the surface area of the wound pad 103. This range allows for sufficient transmission of negative pressure to the wound site and prevents potential gelling particles or larger wound exudate particles from entering the tubing typically connected to the coupling member. In FIG. 1, the tubing attached to the coupling member 104 is denoted 120. The proportions of the first 103a, and the second 103b of the wound pad may vary depending on the size and shape of the dressing. For e.g. a large and rectangular dressing, the proportion of the second portion is typically smaller; i.e. within the lower range, whereas for a small and square shaped dressing, the proportion of the second portion may be larger; i.e. within the higher range specified above.

The wound pad comprising the first and the second portions may be divided into a central portion and an edge portion surrounding the central portion. The second portion 103b is preferably arranged in the edge portion of the wound pad (see e.g. FIG. 2). The central portion may constitute 30-70% of the surface area of the wound pad.

The provision of the second portion 103b of the wound pad in an edge portion is advantageous for manufacturing, packaging and storing purposes.

In FIG. 1b, the second portion 103b of the wound pad is configured to extend across the entire opening in the backing layer. With "extend across" means that the second portion has an extension in an area below the opening 105 of the backing layer 101, not necessarily directly underlying the opening.

For the purpose of securing efficient transmission of negative pressure, yet avoiding blockage and obstructions in the area below the opening (and the coupling member), the second portion 103b of the wound pad 103 is configured to extend across at least 60%, preferably at least 75%, more preferably at least 90% of the cross-sectional area of the opening 105 in the backing layer 101.

Typically, the second portion 103b extends across the entire cross-sectional area of the opening in the backing layer.

The dressing of the present disclosure is by no means limited to a specific shape, but any shape may be utilized depending on the part of the body where the dressing is to be applied. In exemplary embodiments, the dressing is rectangular or square shaped.

FIG. 3a illustrates a rectangular dressing, and FIG. 3b-d illustrate square shaped dressings.

In FIGS. 3a-3d, the wound pad has a lateral (x) and a longitudinal (y) extension. As illustrated in FIG. 3a, the wound pad 103 is contoured by a pair of longitudinal edges 107a-b extending in parallel to each other in the lateral direction and a pair of lateral edges 108a-b extending in parallel to each other in the longitudinal direction, wherein the second portion 103b of the wound pad 103 is arranged along the longitudinal edge 107a of the wound pad 103.

In FIG. 3b, the second portion 103b of the wound pad is arranged along the lateral edge 108a of a generally square shaped wound pad.

In FIG. 3c, the second portion 103b of the wound pad is arranged in an edge portion of the wound pad; i.e. in an upper corner of the wound pad.

In FIG. 3d, the wound pad comprises a strip of the second portion 103b below the opening 105 provided in the backing layer. The second portion is arranged between a first absorbent portion 103a and a second absorbent portion 103c.

The embodiments illustrated in FIGS. 3a-c are generally preferred to simplify the manufacturing of the dressing.

The transmission layer of the second portion 103b of the wound pad 103 preferably comprises a spacer fabric material.

A spacer fabric material is a three dimensional material that is often utilized in negative pressure wound therapy (NPWT) dressings.

The spacer fabric material secures transmission of negative pressure to the wound site and secure that fluid can be transported away from the wound site into the absorbent portion of the wound pad such that the skin can remain relatively dry.

In embodiments, the spacer fabric layer has a thickness of from 1.5 to 4 mm, e.g. from 2 to 3 mm. The basis weight of the spacer fabric may be from 150 to 500 gsm, e.g. from 200 to 350 gsm.

The spacer fabric material typically comprises a top layer and a bottom layer and an interconnecting layer of pile filaments between the top layer and the bottom layer. The interconnecting layer of pile filaments may have a fineness of 200 to 500 denier, e.g. from 250 to 350 denier.

The spacer fabric material is resistant to compression and is configured to withstand pressures exerted on the dressing during use. After a compressive force has been exerted to the dressing, the transmission layer is configured to return to its original shape immediately after removal of the force.

As best illustrated in FIG. 1b and FIG. 2, the dressing 100 may further comprise a liquid spreading layer 109 arranged between the backing layer 101 and the wound pad 103.

The liquid spreading layer 109 is configured to extend across at least 90% of the surface area of the wound pad 103 and is void of an opening. In FIGS. 1b and 2, the liquid spreading layer 109 extends across the entire wound pad 103.

The fact that the liquid spreading layer 109 does not contain any opening prevents gelling particles and undesired larger particulate from entering the coupling member 104 and the tubing connected thereto.

The liquid spreading layer 109 also has the function of improving the spreading of liquid across a large surface area such that moisture can evaporate through the backing layer in a more efficient manner. When the dressing of the present disclosure is utilized in an NPWT system comprising a remote fluid collection means, e.g. a canister, a portion of the wound exudate will be transported away from the dressing to the canister (typically by means of a tubing connecting the dressing with the canister and the negative pressure source). In such cases, the liquid spreading layer 109 secures that any potential back-flow of exudate from the canister to the wound site is spread out across a large surface rather than flowing back towards the wound site in one spot. Accordingly, the wound site is kept relatively dry. In embodiments, the liquid spreading layer 109 comprises a nonwoven.

The nonwoven liquid spreading layer 109 aids in driving the fluid away from the wound site and from the wound pad 103, while at the same time securing that the maximum capacity of the absorbent dressing can be utilized.

The liquid spreading layer 109 may comprise a melt-blown, spunbond or a spunlaced nonwoven. Examples of suitable polymers for use in the nonwoven are polyethylene, polyesters, polypropylene and other polyolefin homopolymers and copolymers. For example, nonwoven webs comprising thermoplastic fibres of polypropylene and polyethylene fibres or mixtures thereof may be used. The webs may have a high content of thermoplastic fibres and contain at least 50%, e.g. at least 70% thermoplastic fibres. The nonwoven may be a mixture of polyester and viscose, e.g. in a 70:30 ratio. The basis weight of the nonwoven may be in the range of from 10 to 80 g/m², e.g. of from 20 to 50 g/m². The liquid spreading layer may also be a spunbond-meltblown or spunbond-meltblown-spunbond (SMS) web.

As illustrated in FIG. 1b, the at least one transmission layer of the second portion 103b of the wound pad is arranged in contact with the liquid spreading layer 109.

Hence, wound exudate transferred through the second, non-absorbent, portion of the wound pad will be distributed and spread by the liquid spreading layer. Also, larger particulate material is prevented from entering the tubing connecting the dressing with the negative pressure source.

The transmission layer of the second portion 103b of the wound pad 103 may be referred to a first transmission layer. As illustrated in FIGS. 1b and 2, the dressing 100 may further comprise a second transmission layer 110, preferably comprising a spacer fabric material, between the adhesive skin contact layer 101 and the wound pad 103.

In embodiments, the second transmission layer 110 extends across the entire surface of the wound pad 103. The second transmission layer 110 is thus arranged below the first and the second portions of the wound pad.

The area underlying the opening and the coupling member of the backing layer may thus be provided with two transmission layers. Both transmission layers preferably comprise a spacer fabric material. The spacer fabric material preferably has the characteristics as described hereinbefore.

Figure 1C:
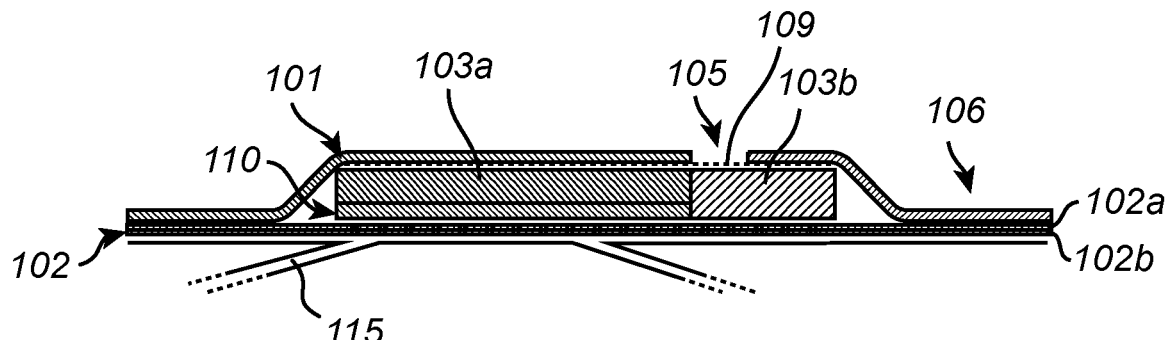
FIG. 1c illustrates a cross-sectional view of a dressing according to an alternative embodiment of the present disclosure

In alternative embodiments, the dressing has the construction as illustrated in FIG. 1c. In FIG. 1c, the second transmission layer 110 is arranged between the adhesive skin-contact layer 102 and the first portion 103a of the wound pad 103, and wherein the second portion 103b of the wound pad has a thickness corresponding to the thickness of the first portion 103a of the wound pad 103 and the second transmission layer 110.

Accordingly, the second portion 103b may comprise one thicker transmission layer arranged between the adhesive skin-contact layer 102 and the liquid spreading layer 109 in the edge portion of the wound pad.

The thickness of the first 103a and the second 103b portion may be in the range of from 1 to 5 mm, preferably in the range of from 2 to 3 mm.

The first absorbent portion 103a may comprise one or a plurality of layers, wherein at least one of the layers is a superabsorbent layer, preferably comprising superabsorbent polymer (SAP) particles.

A "superabsorbent polymer" or "SAP" is a polymer that can absorb up to 300 times its own weight in aqueous fluids. Superabsorbent polymers are constituted by water-swellable and water insoluble polymers capable of absorbing large quantities of fluid upon formation of a hydrogel. The superabsorbent polymers for use in accordance with the present disclosure may be inorganic or organic crosslinked hydrophilic polymers, such as polyvinyl alcohols, polyethylene oxides, crosslinked polyacrylates and the like. Typically, the superabsorbent (SAP) particles comprise sodium acrylate. The SAP material is in the form of particles. The size of the superabsorbent particles may be in the range of from 45 to 850 µm, e.g. from 150 to 600 µm.

It is also conceivable that the superabsorbent layer comprises superabsorbent fibers (SAF).

In exemplary embodiments, the first portion 103a of the wound pad 103 comprises a superabsorbent layer and at least one liquid distribution layer. The superabsorbent layer is configured to absorb and temporary retain exudate before moisture is evaporated from the dressing.

The liquid distribution layer is configured to absorb and distribute liquid flowing from the wound site. The liquid distribution layer may be arranged below the superabsorbent layer. Accordingly, the liquid distribution layer distributes and spreads the wound exudate evenly and over a large surface area such that it can be absorbed by the superabsorbent layer. Alternatively, the liquid distribution layer is arranged above the superabsorbent layer. This way, the liquid distribution layer allows for a greater surface area from which exudate can evaporate from the backing layer.

With reference to FIG. 2, the first portion 103a of the wound pad 103 may comprise a first liquid distribution layer 111, a superabsorbent layer 112 and a second liquid distribution layer 113, wherein the superabsorbent layer 112 is arranged between the first 111 and the second 113 liquid distribution layers.

Wound exudate flowing from the wound site is first distributed across the area of the first liquid distribution layer 111 before being absorbed by the superabsorbent layer 112. The second liquid distribution layer 113 distributes the exudate from the superabsorbent layer 112 such that the exudate is spread over a large area before being evaporated from the backing layer 101 or transported to the remote fluid collection means (where present) by means of the tubing attached to the coupling member 104.

In embodiments, the first liquid distribution layer 111 is arranged below the superabsorbent layer 112 and has a greater liquid distribution capacity than the second liquid distribution layer 113. An absorbent wound pad portion with a liquid distribution gradient is thus achieved, which impacts the ability of the wound pad to retain, and remove, respectively, liquid from and within the dressing.

In embodiments, the first portion 103a of the wound pad is embossed. The embossed absorbent structure improves the fluid handling properties of the dressing and contributes to a balanced and more controlled spreading of wound exudate. Furthermore, the embossed absorbent structure allows the dressing to retain its shape and thinness, while also being pliable.

In embodiments where the dressing is connected to a remote fluid collection means, the first absorbent portion 103a secures a balanced distribution of liquid between the two fluid collection means (the dressing and the remote fluid collection means) such that the wear time of the dressing can be improved.

In such embodiments, it is advantageous that the amount of superabsorbent particles in the first absorbent portion 103a is from 10 to 20 mg/cm2, preferably of from 13 to 17 mg/cm2.

Such an absorbent structure absorbs exudate at a "reasonable" level. If too much SAP is included, the SAP layer may swell and absorb too much and too quickly. This may have the effect that the dressing serves as the sole or at least predominant means for fluid collection. If the NPWT system comprises a remote fluid collection means, the balance between the remotely arranged fluid collection means, e.g. the canister, and the dressing is preferably 50:50, e.g. at least 40:60 or 60:40. This balance may improve the wear time of the dressing.

The absorbent portion 103a may have a basis weight of from 250 to 550 g/m², preferably of from 350 to 450 g/m². This way, the liquid distribution is controlled and a proper balance between liquid absorption and liquid removal from the dressing can be achieved. Furthermore, the dressing is pliable and may adapt to the movement of a wearer in a better way.

The first 111 and/or second 113 liquid distribution layer may comprise any material having the ability to distribute the exudate in an efficient manner. For example, the first and/or second liquid distribution layer comprises a nonwoven material.

For example, the first liquid distribution layer 111 may comprise a nonwoven. The nonwoven may have a grammage in the range of from 20 to 50 gsm, e.g. from 30 to 40 gsm. The thickness of the liquid distribution layer 111 may be from 0.2 to 1.2 mm, e.g. from 0.2 to 0.6 mm.

The second liquid distribution layer 113 may be a tissue or a nonwoven layer. Typically, the liquid distribution capability of the upper layer 113 is lower than the liquid distribution capability of the lower liquid distribution layer 111.

The layer 113 also serves to prevent leakage of SAP particles from the superabsorbent layer 112. The SAP particles of the superabsorbent layer 112 chemically bind exudate entering the superabsorbent layer 112, and thereby forms an aqueous gel. The layer 113 prevents gelling particles from moving towards the backing layer 101 and towards the coupling member 104, typically connected to a tubing. Undesirable blockage of gel particles within the tubing is thereby prevented. The layers 111 or 113 may also serve as a "support layer" and act as a carrier during the manufacturing process.

The various layers of the first absorbent portion 103a create a complex liquid absorption and retention structure and an improved liquid distribution is observed. In embodiments, the portion 103a of the wound pad comprises additional layers.

The superabsorbent layer 112 may be an airlaid superabsorbent layer. In embodiments, the airlaid superabsorbent layer 112 comprises superabsorbent particles, cellulosic fibers and bicomponent fibers.

Such a superabsorbent layer allows for improved liquid handling properties and a proper distribution of liquid. Furthermore, it prevents gel blocking and prevents the absorbent structure from collapsing when large amounts of fluid are handled. The bicomponent fibers act as a bonding agent, providing integrity to the SAP layer, especially in the wet state. The biocomponent fibers may be made of polyethylene and polyethylene terephthalate (PE/PET).

For example, the airlaid superabsorbent layer may comprise:

30-50%, preferably 35-50% by weight of superabsorbent particles
30-50%, preferably 40-50% by weight of cellulosic fibers
3-10%, preferably 5-8% by weight of bicomponent fibers
3-8% by weight of polyethylene.

The adhesive skin contact layer 102 is the lowermost layer of the dressing. The adhesive skin contact layer 102 is configured to detachably adhere the dressing to a dermal surface. In other words, the adhesive skin contact layer 102 is configured to contact the skin or the wound of a wearer. This layer may also be referred to as a "wound contact layer".

The adhesive skin contact layer 102 preferably comprises a silicone gel. An adhesive skin contact layer comprising a silicone gel is skin-friendly and easy to remove without causing trauma. It is sufficiently adherent to skin such that the dressing stays in place, yet is configured to maintain its adherence with repeated removal and re-application.

As illustrated in FIGS. 1b and 1c, the adhesive skin contact layer 102 may comprise two layers. For example, the adhesive skin contact layer 102 may comprise a polymer based film 102a and a silicone gel layer 102b; the silicone gel layer 102b being arranged to contact the skin of a wearer.

The polymer based film 102a is preferably a breathable film and may comprise e.g. polyethylene, polyamide or polyester polyurethane. Preferably, the polymer based film comprises polyurethane. The thickness of the polyurethane film may be from 15 to 100 μm, e.g. from 20 to 80 μm, preferably from 20 to 60 μm.

Examples of suitable silicone gels for use in the adhesive skin contact layer 102 and/or in the silicone gel layer 102b include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive skin contact layer is typically at least 20 μm. The thickness of the adhesive skin contact layer may be from 100 to 200 μm.

The adhesive skin contact layer 102 may comprise a plurality of apertures 114. The apertures 114 extend through the polymer film 102a (if present) and the silicone gel layer 102b. The apertures 114 improve the absorption of body fluids into the dressing 100 without compromising the adhesiveness to the skin area.

The adhesive skin contact layer 102 preferably comprises a plurality of apertures 114 in the area underlying the wound pad 103, but is void of apertures in the area forming the border portion 106. The lack of apertures in the border portion of the dressing is beneficial to improve the adhesion at the border portion 106 of the dressing and thereby improve the stay-on ability of the dressing.

The backing layer 101 is the outermost layer of the dressing and is configured to face away from the skin of a wearer. The backing layer 101 typically comprises a thermoplastic elastomer. A thermoplastic elastomer has the ability to be stretched to moderate elongations, and upon the removal of stress, return to its original shape. Examples of suitable materials comprising thermoplastic elastomer include polyurethane, polyamide and polyethylene. The backing layer may also be a laminate of polyester based nonwoven materials and at least one polyurethane film.

Preferably, the backing layer comprises polyurethane. The thickness of the backing layer may be in the range of from 10 to 40 μm, preferably from 15 to 30 μm. The backing layer 101 may comprise one or more films, optionally laminated together.

Figure 4:
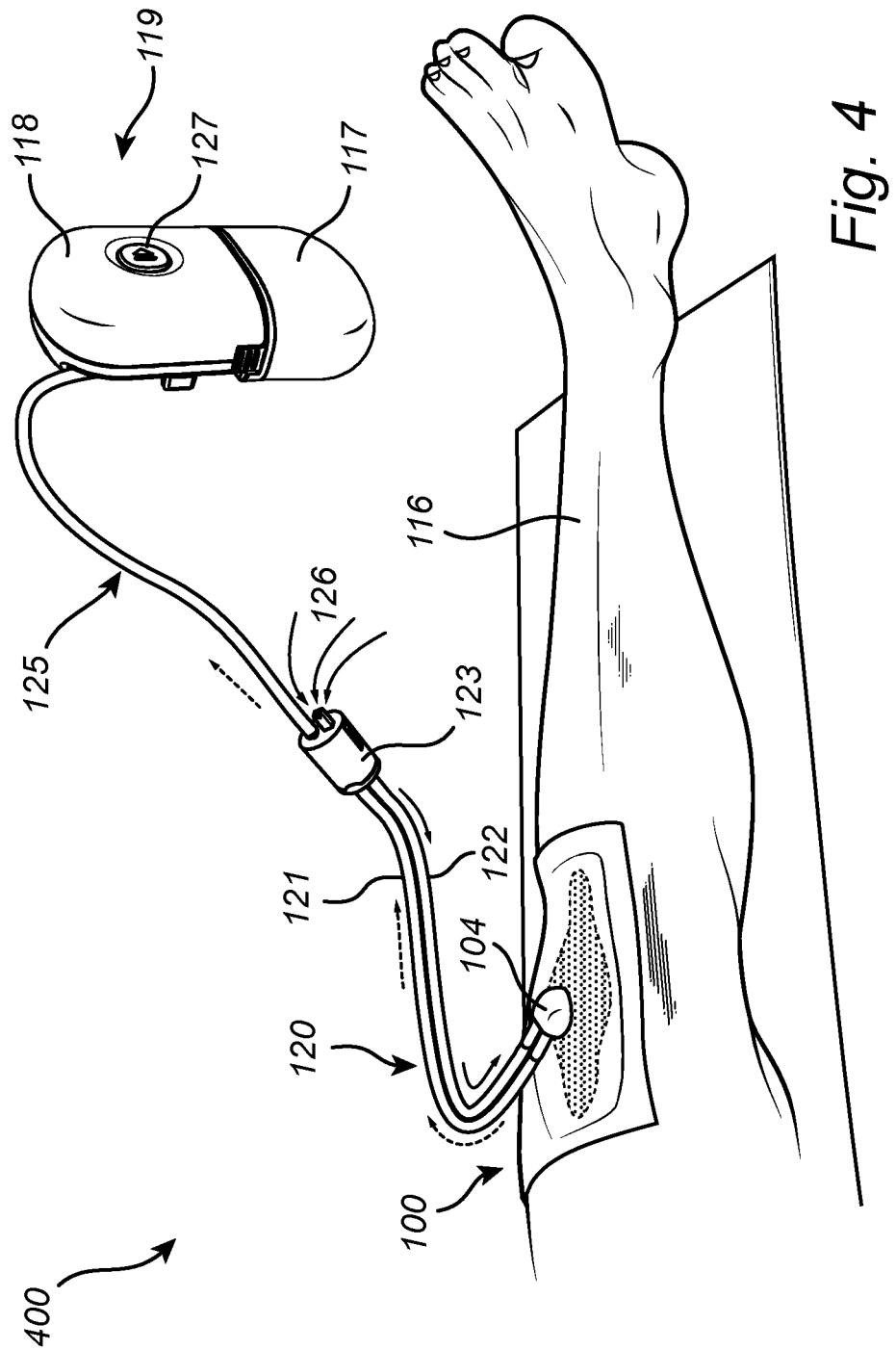
FIG. 4 conceptually illustrates a negative pressure wound therapy (NPWT) system according to an exemplary embodiment of the present disclosure.

A release liner 115 is typically detachably attached to the adhesive skin contact layer 102. The release liner 115 protects the adhesive surface from contamination prior to use. The release liner 115 may comprise two or more release liner portions. With reference to FIG. 4, a negative pressure wound therapy (NPWT) system according to the present disclosure is conceptually illustrated.

The negative pressure wound therapy (NPWT) system 400 comprises:

a negative pressure wound therapy (NPWT) dressing 100 as described hereinbefore, a negative pressure source fluidly connected to the dressing 100.

In FIG. 4, the dressing 100 is applied to the knee of a patient 116.

In the system of FIG. 4, the system 400 further comprises a remote fluid collection means fluidly connected to the negative pressure source and to the dressing 100. The remote fluid collection means is, in FIG. 4, a canister 117.

The negative pressure source is a negative pressure pump adapted for establishing a negative pressure when the negative pressure pump is in an active state. The negative pressure pump may be any type of pump that is biocompatible and maintains or draws adequate and therapeutic vacuum levels. Preferably, the negative pressure level to be achieved is in a range between about −20 mmHg and about −300 mmHg. In embodiments of the present disclosure, a negative pressure range between about −80 mmHg and about −180, preferably between about −100 and −150 mmHg, more preferably between −110 and −140 mmHg is used. In embodiments, the negative pressure pump is a pump of the diaphragmatic or peristaltic type.

As used herein, the term "fluidly connected" is to be interpreted broadly and may comprise e.g. any form of tubing, conduits, or channels providing a fluid connection/communication between the negative pressure source, the remote collection means (if present) and the dressing 100.

Preferably, the remote fluid collection means is a canister 117. Alternatively, it may be an absorbent material present within the tubing of the NPWT dressing or NPWT system or a dressing or absorbent structure arranged between the dressing of the present disclosure and the canister 117.

In FIG. 4, the negative pressure source is comprised within a housing 118 of a portable negative pressure wound therapy (NPWT) device 119. The canister 117 is preferably detachably connected to the housing 118. The detachable configuration allows the user or caregiver to remove the canister 117 and empty the collected liquid, and subsequently re-attach the canister 117 to the housing 118 again.

The canister 117 may be formed from e.g. molded plastic or the like. The canister 117 is preferably at least partly transparent/translucent to permit viewing into the interior of the canister 117 to assist the user in determining the remaining capacity of the canister 117.

An inner volume of the canister 117 may e.g. be between 30-300 ml, e.g between 40 and 150 ml. The inner volume of the canister 117 may vary depending on the type of wound. In embodiments, the canister 117 comprises a liquid absorbent material. In a possible embodiment at least 75% of the inner volume of the canister 117 is occupied with a liquid absorbent material.

The NPWT device 119 may be connected to the dressing 100 by means of a tubing or a tubing assembly.

In FIG. 4, the dressing comprises a first tubing 120 detachably connected or firmly attached to the coupling member 104. In FIG. 4 (and FIG. 1), the first tubing 120 comprises a fluid conduit 121 configured to remove fluid from the dressing and an air conduit 122 configured to supply air to the fluid conduit 121 and/or the dressing 100. Accordingly, the first tubing 120 is a double conduit. This arrangement is beneficial when a remote fluid collection means 117 is utilized in the NPWT system.

The NPWT system further comprises a connector unit 123 at a position between the dressing 100 and the NPWT device 119. The connector unit 123 may comprise a first connector portion (denoted 124 in FIG. 1) and a second connector portion (not shown). The connector portions are preferably detachably connected such that the dressing can be easily disconnected from the NPWT device 119. This is beneficial in portable NPWT systems as the user may decide to disconnect the dressing 100 from the device 119 when he/she is going to take a shower or for some other reason.

The NPWT system 400 comprises a second tubing 125 configured to provide fluid communication between the connector unit 123 and the negative pressure source and the remote fluid collection means 117, if present.

In FIG. 4, the first tubing 120 is a double conduit, whereas the second tubing 125 between the NPWT device 119 and the connector unit 123 is a single conduit. The NPWT system is by no means limited to such a construction, but may comprise a single conduit or a double conduit between the NPWT device 119 and the dressing 100. The NPWT system is also not limited to the use of a connector unit 123. The tubing 120 may, in embodiments, be configured to extend all the way to the NPWT device 119.

The first 120 and the second 125 tubing and/or the coupling member 104 may be comprise any suitable flexible tubing/coupling member fabricated from elastomeric and/or polymeric materials. The first tubing 120 may be firmly or fixedly attached to the coupling member 104. In alternative embodiments, the first tubing 120 is detachably attached to the coupling member 104.

The coupling member 104 typically comprises an attachment portion configured to be attached to the backing layer of the dressing. The coupling member may be adhesively attached to the backing layer. The coupling member may also comprise a fluid inlet and a fluid outlet configured to be connected to the tubing 120; i.e. to the air conduit 122, and to the fluid conduit 121, respectively.

The coupling member may have the construction as defined in EP application Ser. No. 13/152,841.6.

The NPWT system 400 may comprise means to supply air to the dressing at a rate of from 2 to 7 ml/min during operation.

Preferably, the means to supply air to the dressing is configured to supply air at a rate of from 2-7 ml, preferably of from 3-5 ml at a negative pressure of from −80 to −180 mmHg, preferably of from −100 to −150 mmHg, more preferably of from −110 to −140 mmHg.

A small and controlled inflow of air may be beneficial to more efficiently draw fluid from the wound site and transport the fluid to the remotely arranged fluid collection means, e.g. the canister. The introduction of air may resolve potential exudate blockages or liquid columns formed in the tubing.

In the NPWT system 400 illustrated in FIG. 4, ambient air is introduced into the system by means of the connector unit 123 (illustrated by the arrows 126). For example, the first and/or the second connector portion may comprise an air filter (not shown) configured to control the supply of air into the dressing 100 and/or into the first tubing 120. The first and/or the second connector portion may e.g. comprise an air inlet port, wherein the air filter is arranged.

The air filter may comprise a hydrophobic and porous material, wherein the size of the pores is within the range of from 2 to 20 μm, preferably in the range of from 5 to 12 μm. The pore size of the filter is measured in a non-compressed state.

The air filter may comprise polyethylene, preferably sintered polyethylene. A sintered polyethylene filter has a repeating linear molecular structure —CH2-CH2. The structure is inert with strong molecular bonds, and is characterized by improved chemical resistance, light weight, thermoplasticity and good filtering properties. A sintered polyethylene filter is also environmentally friendly as it produces no toxic waste and can be washed off and re-used.

The air filter secures that the supply of air is in the range of from 2-7 ml/min during operation, e.g. at a negative pressure of −80 mmHg to −150 mm Hg, e.g. from −100 mmHg to −130 mmHg.

It should be noted that air may be introduced into the system in alternative ways, and an air filter may be provided at alternative positions in the system. The regulation of air supply may, in embodiments, be controlled by the NPWT device 119.

During use, the dressing 100 is arranged at a wound site of the user/patient, forming a sealed space. The first and the second tubing (120 and 125) are provided to fluidly connect the dressing 100 to the NPWT device 119, e.g. to an inlet port of the NPWT device 119. The NPWT device 119 is then activated, e.g. by the user/patient, by pressing the start/pause button 127. The negative pressure pump is thereby activated. When activated, the negative pressure pump will start to evacuate air through the canister 117, the first and the second tubing (120 and 125) and the sealed space formed by the dressing 100. Accordingly, the negative pressure will be created within the sealed space. In case a liquid has been formed at the wound site, this liquid from the wound site may at least partly be "drawn" from the wound site, through the first and the second tubing (120 and 125), and into the canister 117. The amount of liquid; i.e. exudate that is drawn from the wound and collected in the canister 117 will depend on the type of wound that is being treated as well as the type of wound dressing used. A substantially equal balance between liquid distribution within the dressing and liquid transport to the remote fluid collection means is desired.

A suitable filter member (not shown) may be arranged between the canister 117 and the negative pressure pump to ensure that no liquid is allowed to pass to the negative pressure pump from the canister 117.

Example 1: Absorption Capacity and Liquid Spreading Area

A test was set up to measure the absorption capacity, i.e. the liquid spreading area, of four reference dressings according to the present disclosure when applied in a negative pressure system.

All of the dressings tested comprised, from bottom-to-top, an adhesive skin contact layer (comprising a polyurethane film coated with a silicone gel), a first transmission layer comprising a spacer fabric material, a wound pad comprising at least one first (absorbent portion), and a second portion comprising a second transmission layer comprising a spacer fabric material, a nonwoven liquid spreading layer and a polyurethane backing layer. The first transmission layer and the liquid spreading layer had a cross-sectional area corresponding to that of the entire wound pad. The first (absorbent) portion of the wound pad comprised, from bottom to top, a first nonwoven liquid distribution layer, a superabsorbent layer (comprising superabsorbent particles) and a second tissue liquid distribution layer. An edge portion of the backing layer comprised an opening onto which a coupling member (connecting the dressing by means of tubing to an NPWT device comprising a negative pressure source and a canister) was arranged.

Dressing A was a rectangular dressing with a dressing size of 10×20 cm (with a centralized wound pad, size 5×15 cm), wherein an edge portion of the wound pad was replaced with a spacer fabric layer in the area underlying the opening in the backing layer (5 cm from wound pad edge; wound pad area replaced with spacer fabric: 25 cm2, corresponding to 33% of the total wound pad area). Dressing A generally corresponds to the dressing illustrated in FIG. 3A.

Dressing B was a rectangular dressing with a dressing size of 10×20 cm (with a centralized wound pad, size 5×15 cm), wherein a 2 cm wide strip of the wound pad was replaced with a spacer fabric layer in the area underlying the opening in the backing layer and extending between the lateral edges of the wound pad in the longitudinal direction (wound pad area replaced with spacer fabric: 10 cm2, corresponding to 13.3% of the wound pad area). Dressing B thus had the general construction illustrated in FIG. 3D (except being rectangular in shape).

Dressing C was a square shaped dressing with a dressing size of 25×25 cm (with a centralized wound pad, size 20×20 cm), wherein the corner of the wound pad was replaced with a spacer fabric layer in the area underlying the opening in the backing layer (wound pad area replaced with spacer fabric: 30.3 cm2, corresponding to 7.6% of the total wound pad area. Dressing C had the general construction illustrated in FIG. 3C.

Dressing D was a square shaped dressing with a dressing size of 25×25 cm (with a centralized wound pad, size 20×20 cm), wherein a 2 cm wide strip of the wound pad was replaced with a spacer fabric layer in the area underlying the opening in the backing layer and extending between the lateral edges of the wound pad in the longitudinal direction (wound pad area replaced with spacer fabric: 40 cm2, corresponding to 10% of the total wound pad area). Dressing D had the general construction illustrated in FIG. 3D.

Before measuring spreading area, the dressings were run in an in vitro test setup, including a full negative pressure wound therapy system (pump, canister and dressing) with applied negative pressure (125 mmHg) and with a continuous in flow of test liquid (1,1 g/cm2/24 h which corresponds to 10×20 cm: 250 g/3 days, 25×25 cm: 1320 g/3 days).

Negative pressure was applied to a dressing located on a plexiglass plate, and test liquid was supplied from underneath the dressing using a peristaltic pump. The method controls that negative pressure is distributed from the pressure source to the different parts of the dressing, and that the NPWT system has sufficient fluid handling properties, i.e. wound pad absorption/spreading and transportation to the NPWT device.

The test was run during a total time period of three days (72 hours).

During the test period, photos of the dressings were taken at several occasions, and at the end of the test period, to observe the test liquid absorption behavior; i.e. liquid spreading of the dressings.

After the tests were finalized, the spreading areas of the absorbed test liquid were measured from the photos to evaluate the spreading and absorption pattern of the dressings. The spreading areas were measured by means of planimeter and calibrated ruler and based on a percentage of wet area/dry area across the wound pad.

A planimeter is a tool that is used to measure the area of irregular shapes, which necessitates calculation of complex variables. The planimeter comprises a tracer arm, and when a user moves the tracer arm, an attached measuring wheel carefully traces the outline with the index to calculate the area. The average liquid spreading area, defined as a percentage of wet dressing area, is illustrated in table 1 below (five prototypes tested in each dressing category).

TABLE 1

| Average liquid spreading area of four reference dressings | | | | |
|---|---|---|---|---|
| Time | Average liquid spreading area (% of wet dressing area) | | | |
| (hours) | Dressing A | Dressing B | Dressing C | Dressing D |
| 0 | 0 | 0 | 0 | 0 |
| 5-7 | 13 | 25 | 14 | 16 |

TABLE 1-continued

| Average liquid spreading area of four reference dressings | | | | |
|---|---|---|---|---|
| Time | Average liquid spreading area (% of wet dressing area) | | | |
| (hours) | Dressing A | Dressing B | Dressing C | Dressing D |
| 20-23 | 34 | 61 | 59 | 56 |
| 28-30 | 53 | 67 | 75 | 75 |
| 49-52 | 72 | 78 | 85 | 100 |
| 72 | 91 | 85 | 89 | 100 |

As demonstrated in table 1, all four dressings evaluated exhibited great absorption properties and liquid spreading behavior. The replacement of a non-absorbent portion in a part of the wound pad did not affect the ability of the dressings to handle wound exudate. Instead of flowing directly from the wound site, through the spacer fabric material, wound exudate was properly handled, stored and distributed within the dressings.

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A negative pressure wound therapy (NPWT) dressing comprising:

a backing layer;

an adhesive skin contact layer; and a wound pad arranged between said backing layer and said adhesive skin contact layer, wherein said backing layer comprises a coupling member configured to connect the dressing to a negative pressure source, wherein said backing layer comprises an opening in the area where the coupling member is attached, wherein said wound pad comprises a first portion comprising one or more absorbent layers and a second portion comprising at least one transmission layer, wherein said second portion of said wound pad is arranged below said coupling member, wherein the one or more absorbent layers comprise a first absorbent layer having a first lateral edge and a second lateral edge that are spaced along a first axis that is perpendicular to a thickness of the one or more absorbent layers, wherein the at least one transmission layer comprises a first transmission layer having a first lateral edge and a second lateral edge that are spaced along the first axis, and wherein both the first and second lateral edges of the transmission layer are positioned on a first side of the second lateral edge of the first absorbent layer along the first axis.

2. The negative pressure wound therapy (NPWT) dressing according to claim 1, wherein said first portion and said second portion of said wound pad form two distinct, juxtaposed portions arranged in the same plane.

3. The negative pressure wound therapy (NPWT) dressing according to claim 1, wherein said first portion of said wound pad comprises a superabsorbent material wherein said second portion of said wound pad is void of a superabsorbent material.

4. The negative pressure wound therapy (NPWT) dressing according to claim 1, wherein said first portion constitutes from 60% to 95% of the surface area of said wound pad.

5. The negative pressure wound therapy (NPWT) dressing according to claim 1, wherein said wound pad comprises a central portion and an edge portion surrounding said central portion, and wherein said second portion is arranged in said edge portion of said wound pad.

6. The negative pressure wound therapy (NPWT) dressing according to claim 1, wherein said second portion of said wound pad is configured to extend across at least 60% of the cross-sectional area of said opening in said backing layer.

7. The negative pressure wound therapy (NPWT) dressing according to claim 1, wherein said wound pad has a lateral (x) and a longitudinal (y) extension and wherein said wound pad is contoured by a pair of longitudinal edges extending in parallel to each other in the lateral direction and a pair of lateral edges extending in parallel to each other in the longitudinal direction, wherein said second portion of said wound pad is arranged along one of said longitudinal edges or along one of said lateral edges of said wound pad.

8. The negative pressure wound therapy (NPWT) dressing according to claim 1, wherein said dressing further comprises a liquid spreading layer arranged between said backing layer and said wound pad.

9. The negative pressure wound therapy (NPWT) dressing according to claim 8, wherein said liquid spreading layer is configured to extend across at least 90% of the surface area of said wound pad and wherein said liquid spreading layer is void of an opening.

10. The negative pressure wound therapy (NPWT) dressing according to claim 8, wherein said liquid spreading layer comprises a nonwoven.

11. The negative pressure wound therapy (NPWT) dressing according to claim 8, wherein said at least one transmission layer of said second portion is arranged in contact with said liquid spreading layer.

12. The negative pressure wound therapy (NPWT) dressing according to claim 1, wherein said transmission layer of said second portion of said wound pad is a first transmission layer and wherein said dressing further comprises a second transmission between said adhesive skin contact layer and said wound pad.

13. The negative pressure wound therapy (NPWT) dressing according to claim 12, wherein said second transmission layer is arranged between said adhesive skin-contact layer and said first portion of said wound pad, and wherein said second portion of said wound pad has a thickness corresponding to the thickness of said first portion of said wound pad and said second transmission layer.

14. The negative pressure wound therapy (NPWT) dressing according to claim 1, wherein said first portion of said wound pad comprises a first liquid distribution layer, a superabsorbent layer and a second liquid distribution layer, wherein said superabsorbent layer is arranged between said first and said second liquid distribution layers.

15. A portable negative pressure wound therapy (NPWT) system comprising:

a negative pressure wound therapy (NPWT) dressing according to claim 1 and a negative pressure source fluidly connected to said dressing.

16. The portable negative pressure wound therapy (NPWT) system according to claim 15, wherein said system further comprises a remote fluid collection canister fluidly connected to said negative pressure source and to said dressing.

17. The portable negative pressure wound therapy (NPWT) system according to claim 16, wherein said system comprises an air inlet configured to supply air to said dressing at a rate from 2 to 7 ml/min during operation.

\*    \*    \*    \*    \*